(12) United States Patent
Ushiba et al.

(10) Patent No.: US 10,223,784 B2
(45) Date of Patent: Mar. 5, 2019

(54) PATTERN EVALUATION DEVICE AND VISUAL INSPECTION DEVICE COMPRISING PATTERN EVALUATION DEVICE

(71) Applicant: Hitachi High-Technologies Corporation, Minato-ku, Tokyo (JP)

(72) Inventors: Hiroyuki Ushiba, Tokyo (JP); Tsuyoshi Minakawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/761,154

(22) PCT Filed: Jan. 27, 2014

(86) PCT No.: PCT/JP2014/051661
§ 371 (c)(1),
(2) Date: Jul. 15, 2015

(87) PCT Pub. No.: WO2014/119509
PCT Pub. Date: Aug. 7, 2014

(65) Prior Publication Data
US 2016/0063690 A1 Mar. 3, 2016

(30) Foreign Application Priority Data

Jan. 29, 2013 (JP) .................................. 2013-013826

(51) Int. Cl.
*G06T 7/00* (2017.01)
*G01N 21/956* (2006.01)
(Continued)

(52) U.S. Cl.
CPC ......... *G06T 7/001* (2013.01); *G01N 21/8851* (2013.01); *G01N 21/9501* (2013.01);
(Continued)

(58) Field of Classification Search
CPC ...... G06T 7/001; G06K 9/00; G01N 21/9501; G01N 21/8851; G01N 21/956; G01N 21/95607; G03F 7/70466; G01B 2210/56
(Continued)

(56) References Cited

U.S. PATENT DOCUMENTS

2008/0286885 A1 11/2008 Izikson et al.
2009/0238441 A1 9/2009 Yamashita
(Continued)

FOREIGN PATENT DOCUMENTS

JP          6-185999 A     7/1994
JP     2009-222626 A    10/2009
(Continued)

OTHER PUBLICATIONS

International Search Report (PCT/ISA/210) dated Apr. 1, 2014 (Two (2) pages).
(Continued)

*Primary Examiner* — Ruiping Li
(74) *Attorney, Agent, or Firm* — Crowell & Moring LLP

(57) ABSTRACT

A pattern evaluation device of the present invention includes a model estimation unit that estimates a model caused by a manufacturing method on the basis of an inspection image, a deformation amount estimation unit that estimates a deformation amount of the inspection image by using the estimated model, a reference data deformation unit that deforms reference data by using the estimated deformation amount, and an evaluation unit that performs an evaluation process by comparing the reference data which is deformed by the reference data deformation unit with the inspection image.

14 Claims, 15 Drawing Sheets

(51) Int. Cl.
*G01N 21/88* (2006.01)
*G01N 21/95* (2006.01)
*G06K 9/00* (2006.01)
*H01L 21/033* (2006.01)
*H01L 21/66* (2006.01)

(52) U.S. Cl.
CPC ..... *G01N 21/956* (2013.01); *G01N 21/95607* (2013.01); *G06K 9/00* (2013.01); *G01N 2021/8887* (2013.01); *G06T 2207/30148* (2013.01); *H01L 21/0337* (2013.01); *H01L 22/12* (2013.01)

(58) Field of Classification Search
USPC ........................................................ 382/154
See application file for complete search history.

(56) References Cited

U.S. PATENT DOCUMENTS

2011/0047518 A1  2/2011  Aiba et al.
2012/0267528 A1*  10/2012  Sakai .................. G03F 7/70466
                                                          250/307
2012/0328181 A1*  12/2012  Kitamura .................. G06K 9/00
                                                          382/145

FOREIGN PATENT DOCUMENTS

JP    2010-537394 A    12/2010
JP    2011-43672 A     3/2011
JP    2012-2663 A      1/2012
JP    2013-236031 A    11/2013

OTHER PUBLICATIONS

Japanese language Written Opinion (PCT/ISA/237) dated Apr. 1, 2014 (Five (5) pages).

* cited by examiner

[Fig. 1]
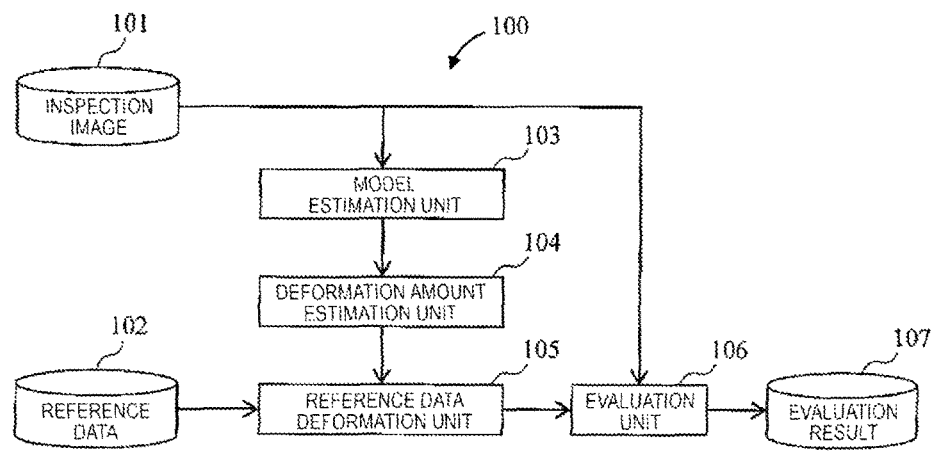
[Fig. 2]
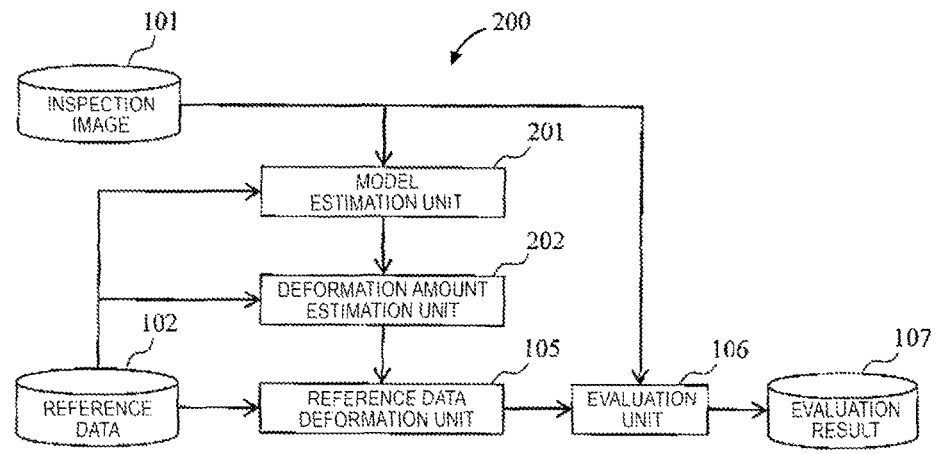

[Fig. 3]
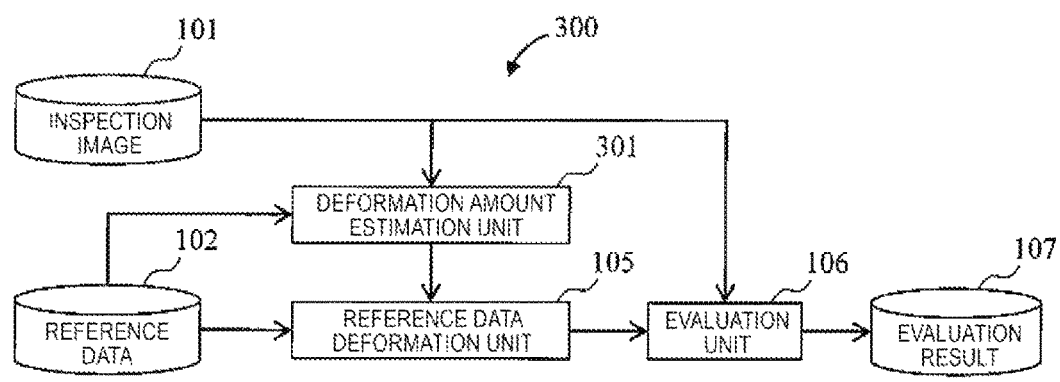

[Fig. 4A]
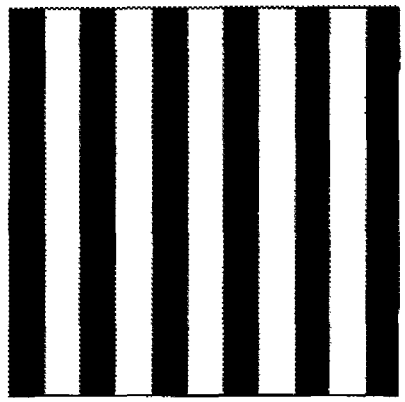
LINE PATTERN
[Fig. 4B]
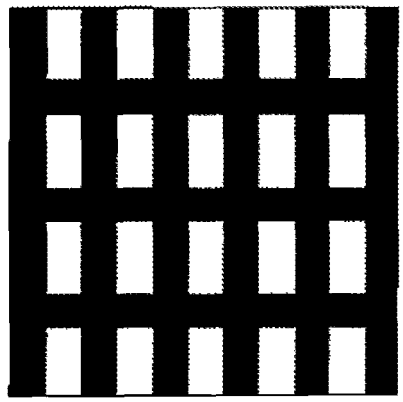
LATTICE PATTERN
[Fig. 4C]
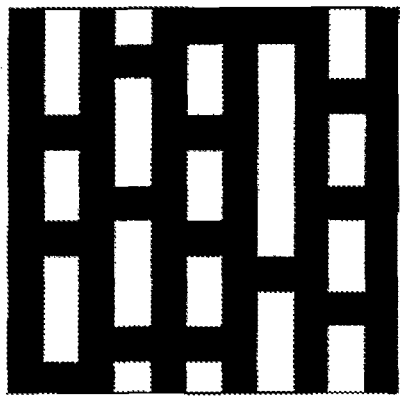
GRID PATTERN
[Fig. 4D]
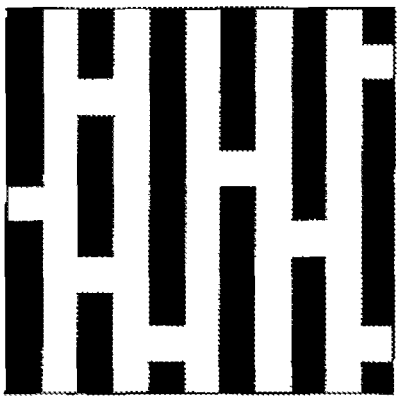
BRIDGE PATTERN
[Fig. 4E]
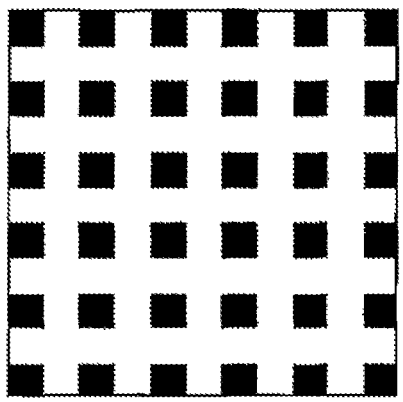
HOLE PATTERN
[Fig. 4F]
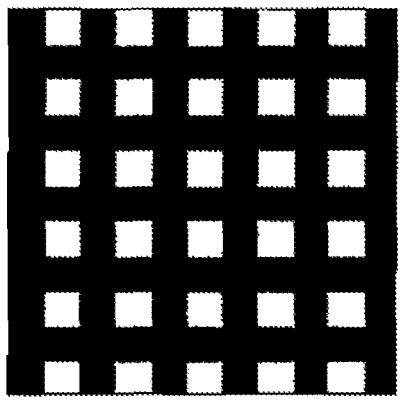
PILLAR PATTERN

[Fig. 5]
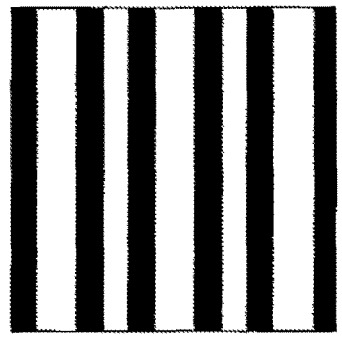
[Fig. 6A]
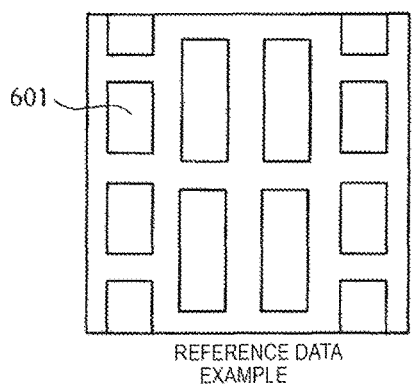
REFERENCE DATA EXAMPLE
[Fig. 6B]
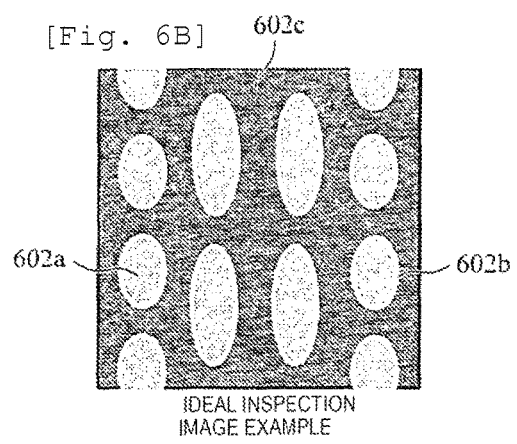
IDEAL INSPECTION IMAGE EXAMPLE
[Fig. 6C]
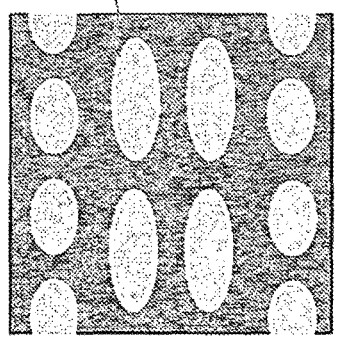
DEFORMED INSPECTION IMAGE EXAMPLE
[Fig. 6D]
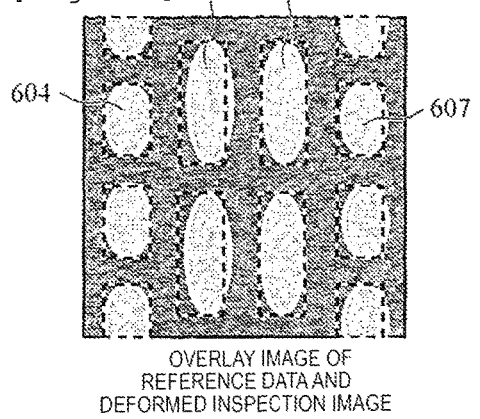
OVERLAY IMAGE OF REFERENCE DATA AND DEFORMED INSPECTION IMAGE

[Fig. 7]
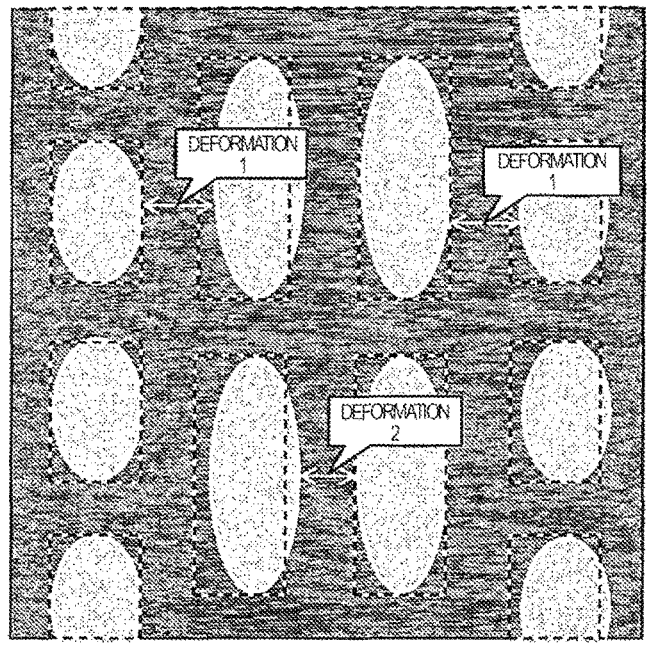
[Fig. 8]
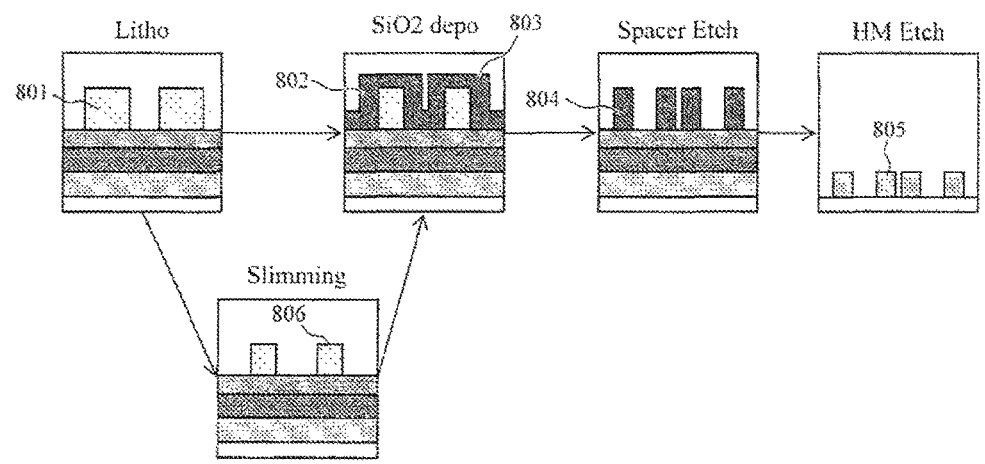

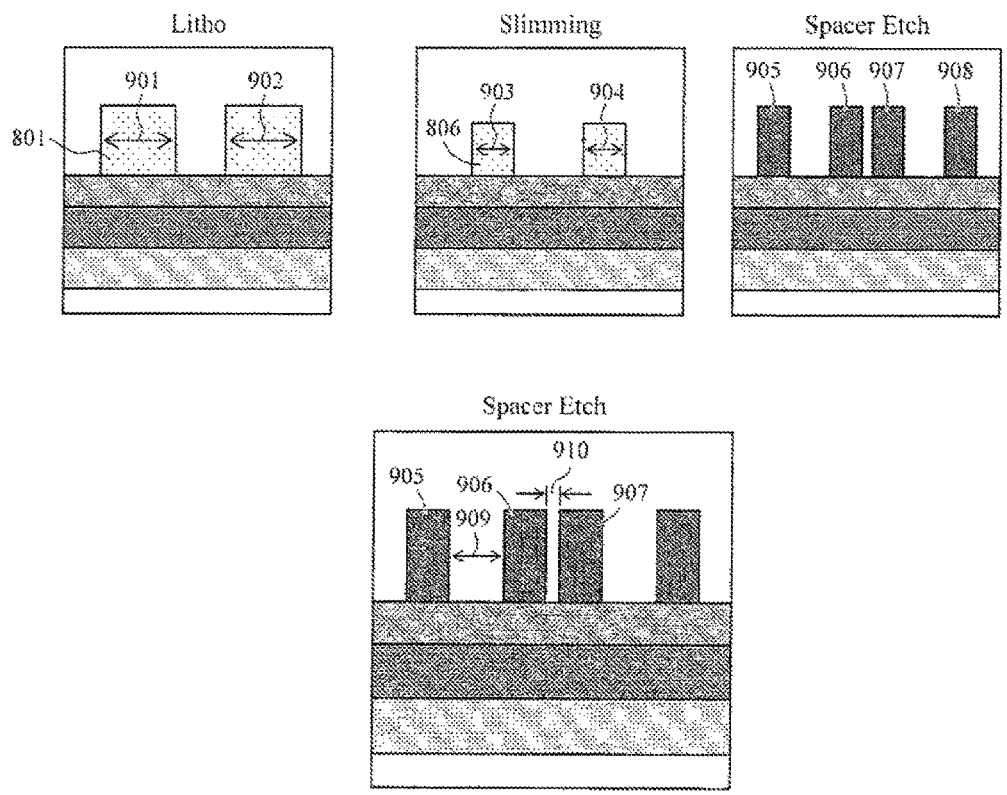
[Fig. 9]

[Fig. 10]
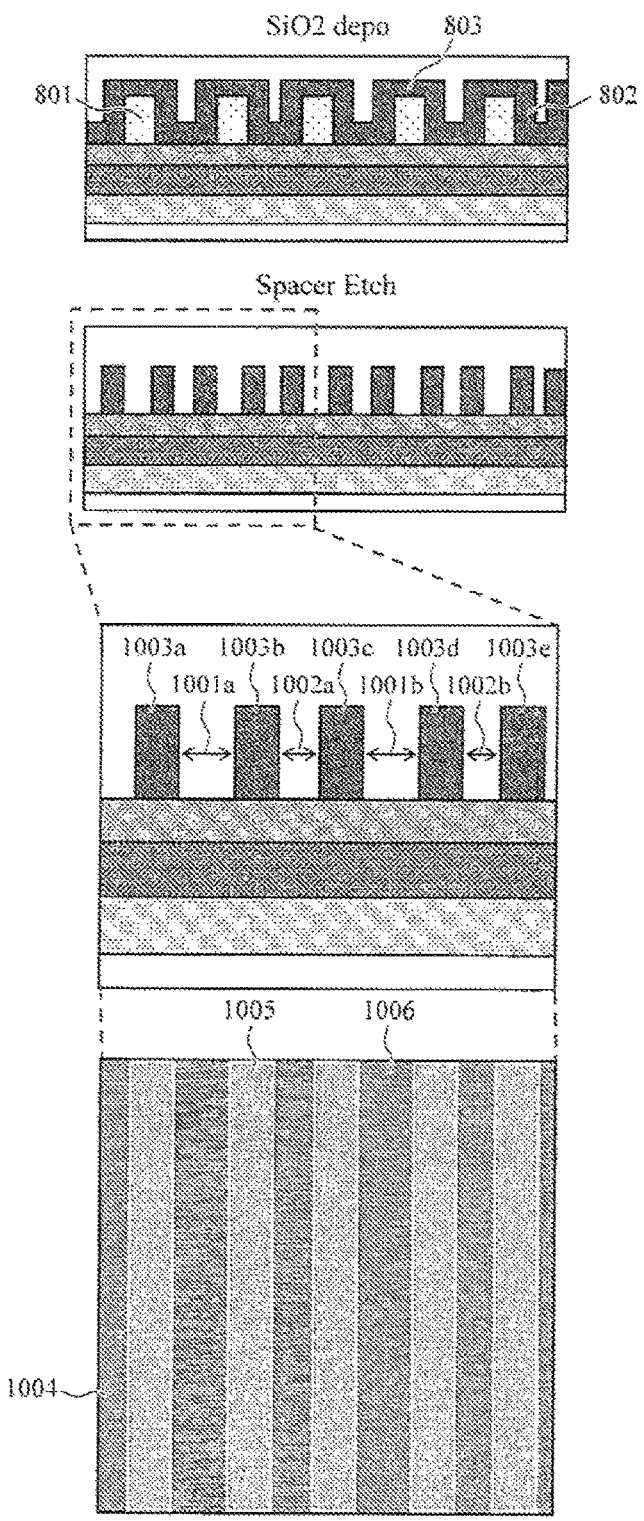

[Fig. 11]
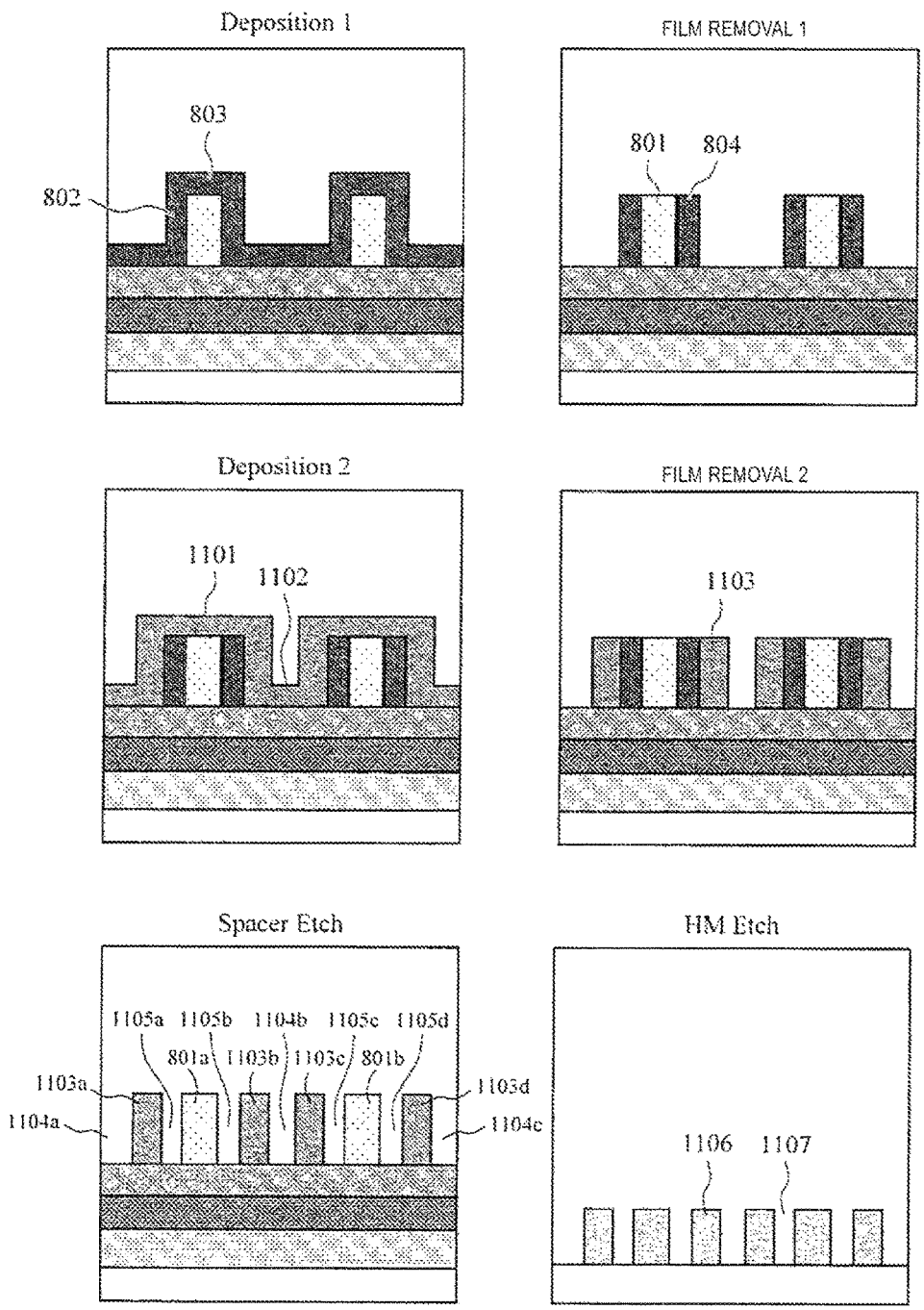

[Fig. 12]
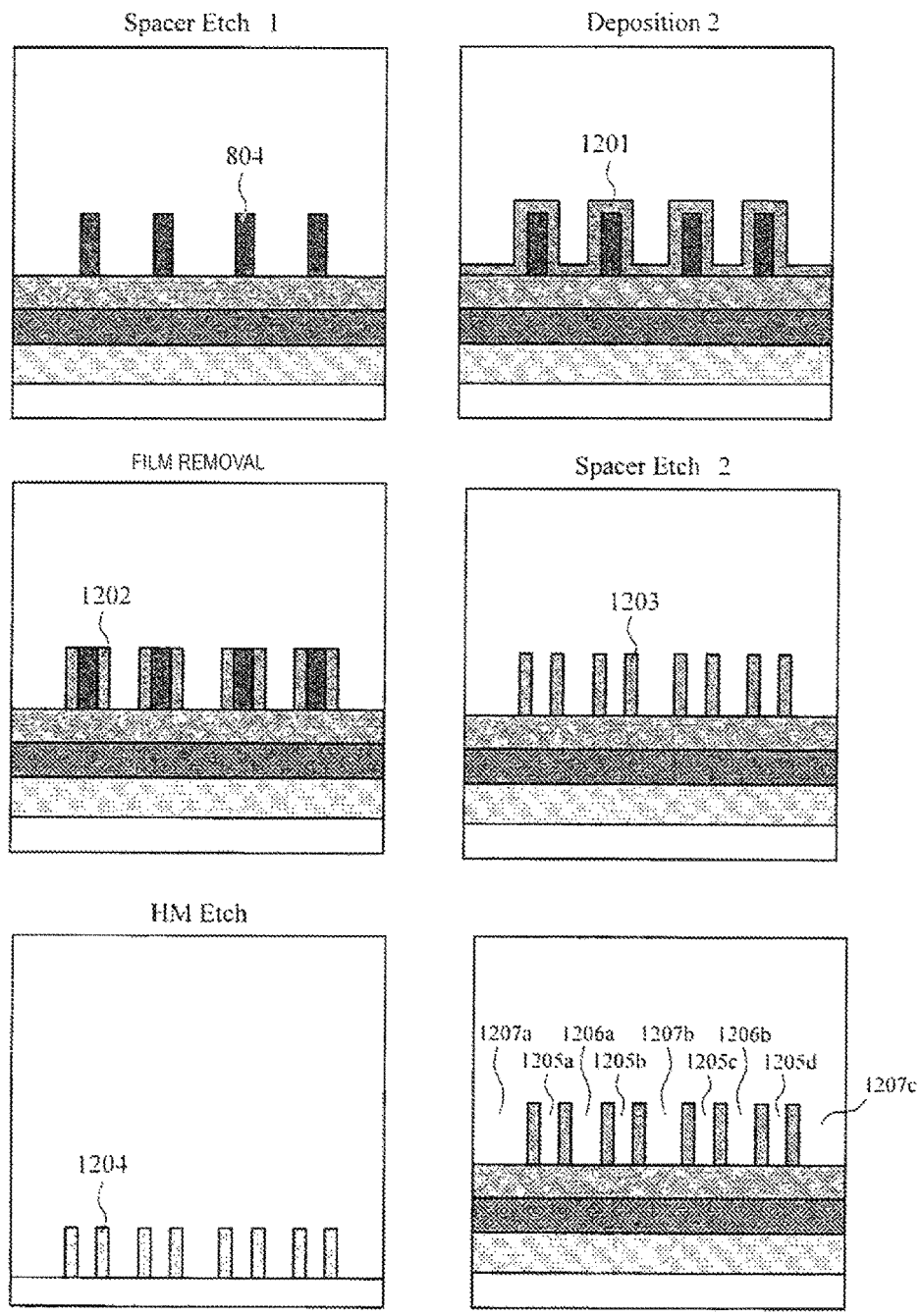

[Fig. 13]
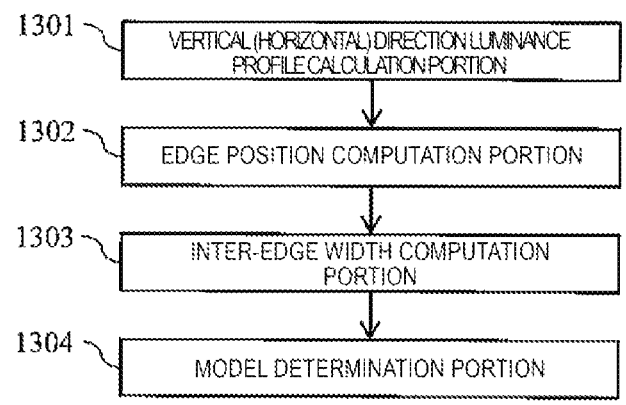
[Fig. 14]
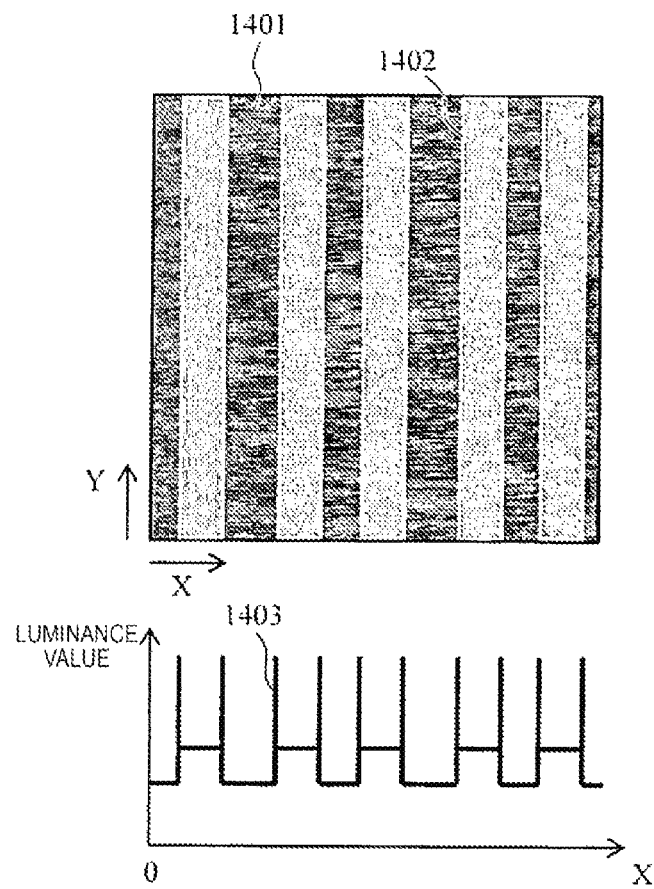

[Fig. 15]
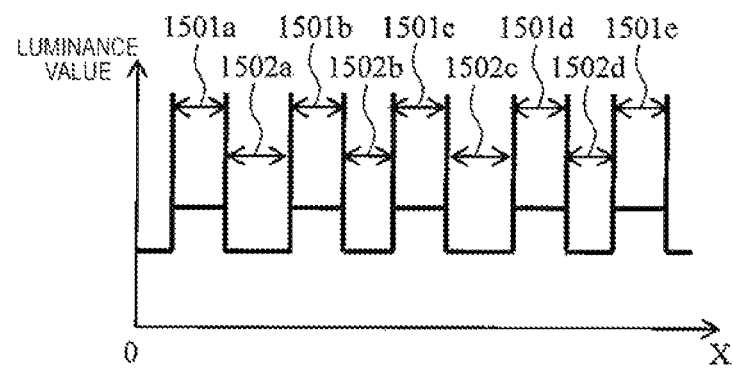
[Fig. 16]
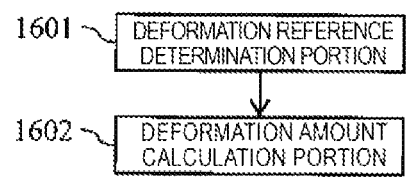

[Fig. 17]
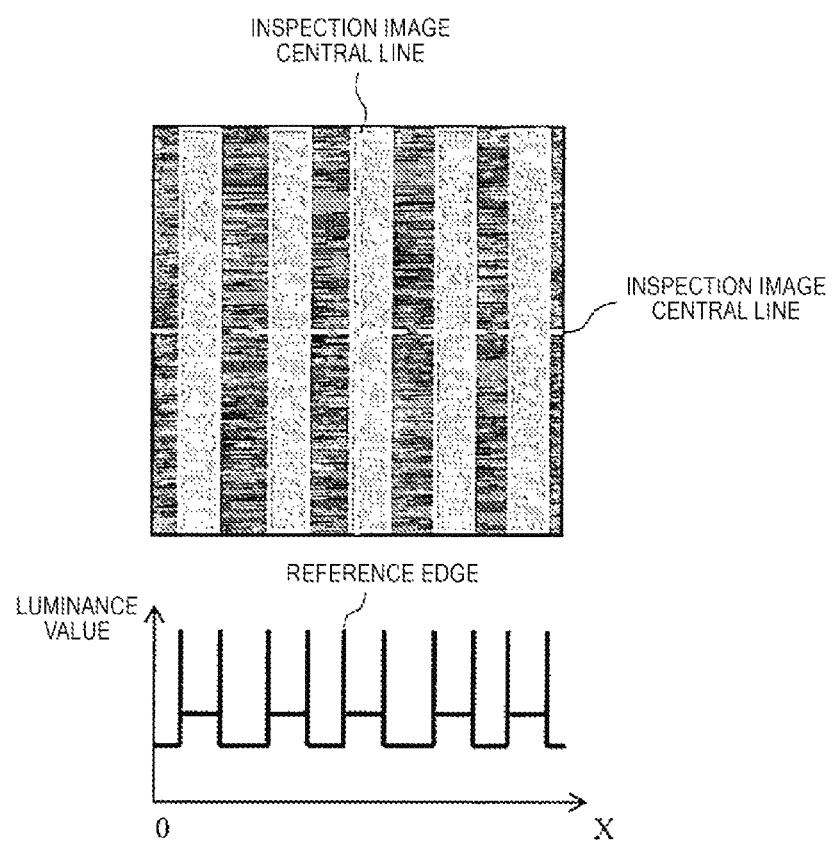

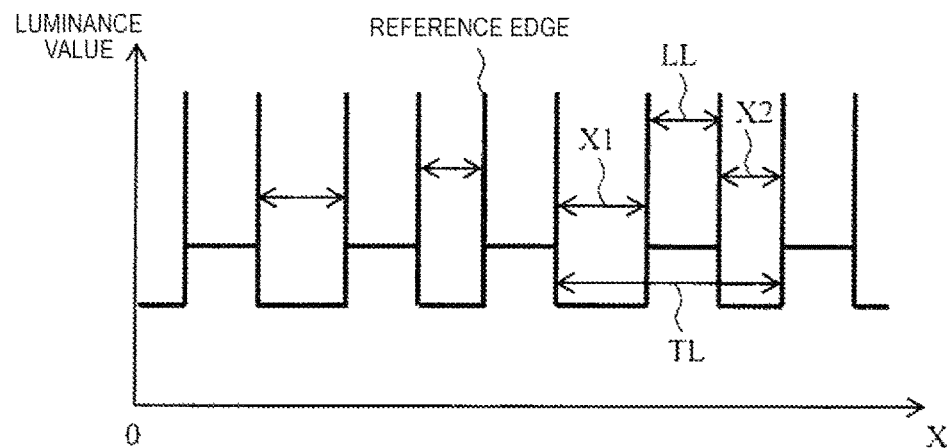
[Fig. 18A]
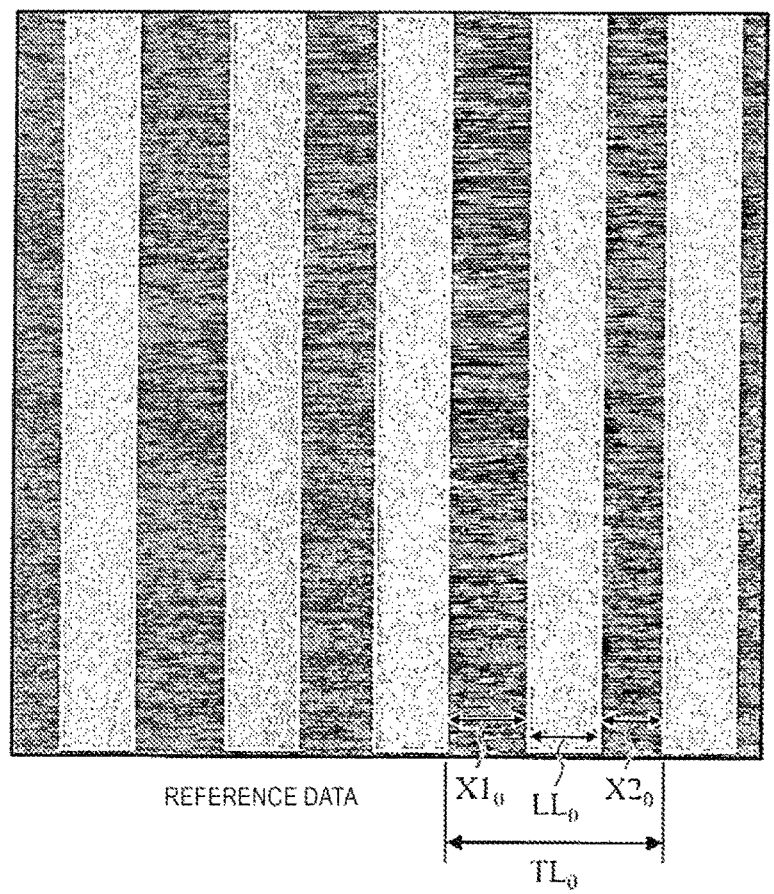
[Fig. 18B]

[Fig. 19]
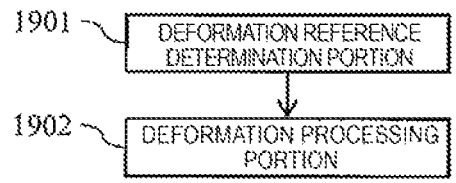
[Fig. 20]
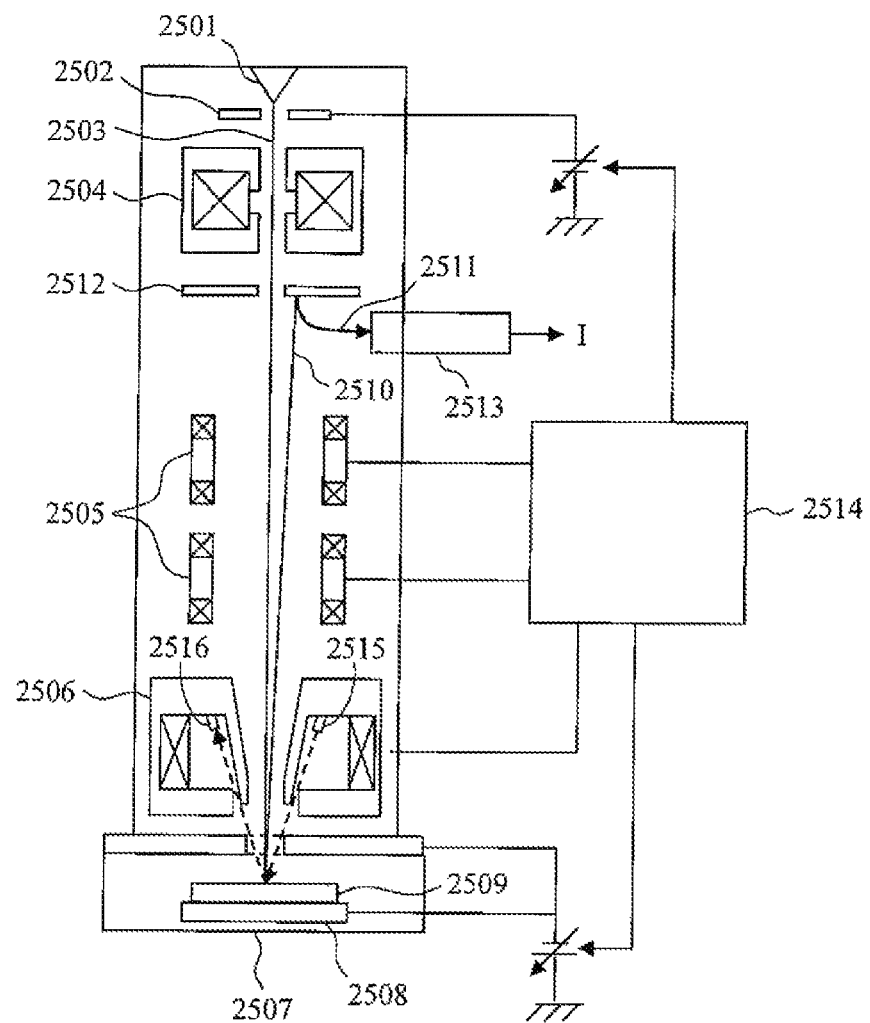

[Fig. 21]
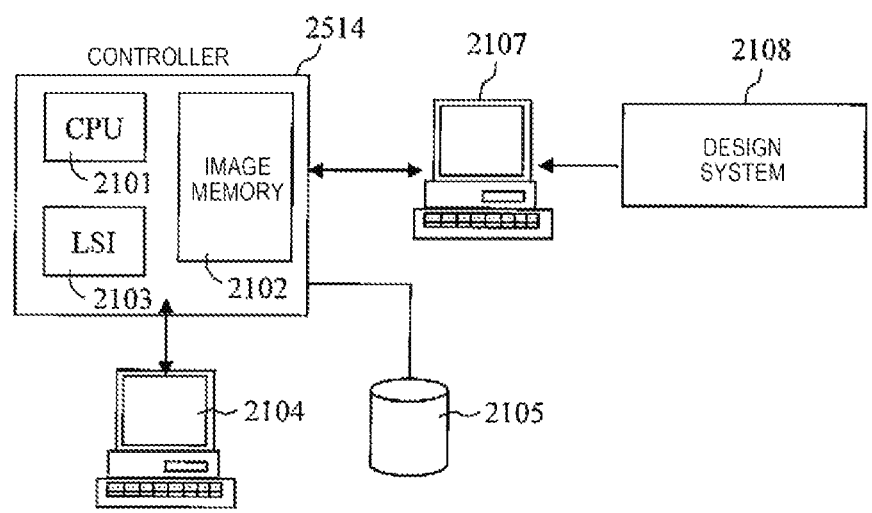

PATTERN EVALUATION DEVICE AND VISUAL INSPECTION DEVICE COMPRISING PATTERN EVALUATION DEVICE

TECHNICAL FIELD

The present invention relates to an image processing device which processes an image signal obtained by a visual inspection device or the like, and particularly to a pattern evaluation device which evaluates performance of an inspection image captured by a visual inspection device, and the visual inspection device including the pattern evaluation device.

BACKGROUND ART

In the related art, as visual inspection devices for semiconductor, there are a device (hereinafter, referred to as an "optical microscope") which applies visible light and uses an image formed by reflected light, and a device (for example, a scanning electron microscope (SEM)) which scans a sample surface with a charged particle beam (whose representative is an electron) and uses an electron which is secondarily generated.

As methods of performing evaluation through shape inspection or dimension measurement of a circuit pattern, there is a method of performing evaluation through comparison between a good quality image which is created in advance and an inspection image (captured image), or a method of performing evaluation through comparison between design data or the like of an inspection target and an inspection image.

Particularly, in a case of performing evaluation by using design data or the like, in order to compensate for a difference in performance between an actually captured image and an inspection target image, a deformation amount is obtained from the captured image, and the design data is deformed on the basis of the deformation amount so that the inspection target image is similar to the captured image, thereby performing inspection (PTL 1).

CITATION LIST

Patent Literature

PTL 1: JP-A-6-185999

SUMMARY OF INVENTION

Technical Problem

However, in the above-described method of obtaining a deformation amount from the captured image, a deformation amount is comprehensively obtained regardless of a difference between deformation caused by a variation in performance due to a manufacturing step and deformation caused by a defect due to layout design of a circuit pattern or a randomly occurring defect. For this reason, design data may be considerably deformed, and thus the reliability of an evaluation result may be notably reduced.

The present invention has been made in consideration of these circumstances, and provides a pattern evaluation technique of obtaining only deformation caused by layout design of a circuit pattern and evaluating the circuit pattern.

Solution to Problem

In order to achieve the object, for example, a configuration disclosed in the claims is employed. The present application includes a plurality of solutions to the problems, and, as an example, there is provided a pattern evaluation device which evaluates performance of an inspection image by using reference data, the device including a model estimation unit that estimates a shape deformation model caused by a manufacturing method on the basis of the inspection image; a deformation amount estimation unit that estimates a deformation amount of the inspection image by using the estimated shape deformation model; a reference data deformation unit that deforms the reference data by using the estimated deformation amount; and an evaluation unit that performs an evaluation process by comparing the reference data which is deformed by the reference data deformation unit with the inspection image. In addition, as another example, there is provided a visual inspection device including the pattern evaluation device.

Advantageous Effects of Invention

According to the present invention, it is possible to perform evaluation which allows deformation of a pattern to an extent of not being defective due to a manufacturing step, and considers only shape deformation which occurs due to a design layout or at random. Consequently, the reliability of pattern evaluation is improved.

Other features related to the present invention will become apparent from the description of the present specification and the accompanying drawings. In addition, objects, configurations, and effects other than the above description will become apparent from the description of the following embodiments.

BRIEF DESCRIPTION OF DRAWINGS

FIG. 1 is a diagram illustrating a configuration of a pattern evaluation device according to a first embodiment of the present invention.

FIG. 2 is a diagram illustrating a configuration of a pattern evaluation device according to a second embodiment of the present invention.

FIG. 3 is a diagram illustrating a configuration of a pattern evaluation device according to a third embodiment of the present invention.

FIGS. 4A-4F are diagrams illustrating a representative example of a circuit pattern created through SAxP.

FIG. 5 is a diagram illustrating another circuit pattern layout which is manufactured.

FIGS. 6A-6D illustrate examples of reference data, an inspection image, and deformation of the inspection image.

FIG. 7 is an enlarged view of FIG. 6.

FIG. 8 illustrates an example of manufacturing steps of a circuit pattern using SADP and illustrates the manufacturing steps by using wafer sectional views.

FIG. 9 illustrates a relationship between widths of a line part and a spacer part of the circuit pattern.

FIG. 10 illustrates a case where a circuit pattern is created through the SADP, and illustrates a relationship between widths of a line part and a spacer part of the circuit pattern.

FIG. 11 illustrates an example of manufacturing steps of a circuit pattern using SATP and illustrates the manufacturing steps by using wafer sectional views.

FIG. 12 illustrates an example of manufacturing steps of a circuit pattern using SAQP and illustrates the manufacturing steps by using wafer sectional views.

FIG. 13 is a diagram illustrating a configuration of a model estimation unit and a process flow.

FIG. 14 illustrates a luminance profile in relation to an SEM image of a line pattern.

FIG. 15 illustrates an example in which peaks are calculated by using the luminance profile, and adjacent peaks are calculated as a width between edges.

FIG. 16 is a diagram illustrating a configuration of a deformation amount estimation unit and a process flow.

FIG. 17 illustrates an example of a method of determining a reference edge.

FIGS. 18A and 18B illustrate a method of estimating a deformation amount.

FIG. 19 is a diagram illustrating a configuration of a reference data deformation unit and a process flow.

FIG. 20 is a diagram illustrating a configuration of a scanning electron microscope.

FIG. 21 is a diagram illustrating a configuration of a controller.

DESCRIPTION OF EMBODIMENTS

Hereinafter, embodiments of the present invention will be described with reference to the accompanying drawings. In addition, the accompanying drawings illustrate specific embodiments conforming to the principle of the present invention, but are only for better understanding of the present invention and are not intended to limit the present invention.

As a visual inspection device, there are an optical microscope which applies visible light and uses an image formed by reflected light, and a charged particle beam device which scans a sample surface with a charged particle beam and uses an electron which is secondarily generated. Examples of the charged particle beam device may include an electron microscope, an electron beam drawing device, an ion processing device, and an ion microscope. The present invention is applicable to the above-described optical microscope and charged particle beam device.

A pattern evaluation device for a visual inspection device related to the present invention evaluates performance of an inspection image by using reference data such as design data. The pattern evaluation device may be realized by an image processing device using a general purpose computer.

The pattern evaluation device includes a central calculation processing device, an auxiliary storage device, a main storage device, and input and output devices. For example, the central arithmetic processing device is constituted of a processor (or a calculation unit) such as a central processing unit (CPU). For example, the auxiliary storage device is a hard disk, the main storage device is a memory, and the input and output devices are a keyboard, a pointing device (a mouse or the like), a display, a LAN port, a USB port, and the like.

A processing unit of the pattern evaluation device described below may be realized by a function of a program which is executed on a computer. In other words, processes described below may be stored in the memory as program codes, and may be realized by the CPU executing the respective program codes. In addition, the processing unit described below may be realized by hardware, for example, by designing the processing unit as an integrated circuit. Further, a storage unit of the pattern evaluation device described below may be realized by the above-described auxiliary storage device or main storage device.

FIG. 1 is a diagram illustrating a configuration of a pattern evaluation device 100 according to a first embodiment of the present invention. The pattern evaluation device 100 includes an inspection image storage unit 101, a reference data storage unit 102, a model estimation unit 103, a deformation amount estimation unit 104, a reference data deformation unit 105, an evaluation unit 106, and an evaluation result storage unit 107.

An inspection image stored in the inspection image storage unit 101 is a captured image which is obtained by the visual inspection device, and is, for example, a captured image of a semiconductor circuit pattern. Reference data stored in the reference data storage unit 102 is, for example, design data of a semiconductor, or an inspection image which is normally created and is called a golden pattern. In other words, the reference data is data used to evaluate performance of an inspection image through comparison with the inspection image. In addition, the reference data may include additional information such as manufacturing step information or visual field deviation information.

An inspection image is input to the model estimation unit 103 from the inspection image storage unit 101, and the model estimation unit 103 estimates a shape deformation model caused by a manufacturing method on the basis of the input inspection image. The shape deformation model will be described later. In addition, the deformation amount estimation unit 104 estimates a deformation amount of the inspection image on the basis of an output from the model estimation unit 103. Further, reference data is input to the reference data deformation unit 105 from the reference data storage unit 102, and the reference data deformation unit 105 modifies the input reference data on the basis of an output from the deformation amount estimation unit 104. The evaluation unit 106 evaluates a semiconductor circuit pattern by comparing the inspection image from the inspection image storage unit 101 with deformed reference data which is output from the reference data deformation unit 105. An evaluation result in the evaluation unit 106 is finally stored in the evaluation result storage unit 107.

FIG. 2 is a diagram illustrating a configuration of a pattern evaluation device 200 related to a second embodiment of the present invention. In FIG. 2, the same constituent elements as in FIG. 1 are given the same reference numerals, and constituent elements other than constituent elements described below perform the same processes as those of the first embodiment illustrated in FIG. 1.

Reference data is input to a model estimation unit 201 and a deformation amount estimation unit 202 illustrated in FIG. 2 from the reference data storage unit 102. The model estimation unit 201 estimates a model of an inspection image by using the reference data information. In addition, the deformation amount estimation unit 202 calculates a deformation amount by using the reference data information. Consequently, it is possible to improve accuracy of estimation of a model and calculation of a deformation amount.

FIG. 3 is a diagram illustrating a configuration of a pattern evaluation device 300 related to a third embodiment of the present invention. In FIG. 3, the same constituent elements as in FIG. 1 are given the same reference numerals, and constituent elements other than constituent elements described below perform the same processes as those of the first embodiment illustrated in FIG. 1.

In FIG. 3, reference data of the reference data storage unit 102 also includes information regarding a shape deformation model. In this case, as illustrated in FIG. 3, the model estimation unit 103 illustrated in FIG. 1 may be omitted. In this case, a deformation amount estimation unit 301 performs processes other than the estimation performed by the model estimation unit 103. In addition, the deformation amount estimation unit 301 calculates a deformation amount by using the reference data information. As mentioned above, the reference data includes the information regarding a deformed model, and a deformation amount is estimated by using the reference data so that estimation performance of a deformation amount can be further improved.

Hereinafter, first, a description will be made of a model for estimating a deformation amount used in the present invention.

The present invention can be used to evaluate a circuit pattern of a semiconductor wafer which is created by using a manufacturing technique of creating a circuit pattern through formation of a sidewall, such as self-aligned double patterning (hereinafter, referred to as SADP), self-aligned triple patterning (hereinafter, referred to as SATP), or self-aligned quadruple patterning (hereinafter, referred to as SAQP) which is one of semiconductor manufacturing techniques.

The SADP, the SATP, and the SAQP are kinds of lithography techniques called double patterning or multiple patterning, and enable creation of a fine and highly dense circuit pattern beyond a limit of ArF immersion exposure. The SADP, the SATP, the SAQP, and a technique can be realized by combining the one or more techniques with each other are hereinafter collectively referred to as SAxP. In the SAxP, a deformation rule of a circuit pattern which is created separately can be modeled. In addition, the SAxP is used to create a specific circuit pattern to be described later, such as a line pattern by forming a sidewall.

FIG. 4 illustrates representative examples of a circuit pattern created through the SAxP. Main circuit patterns created through the SAxP include (a) a line pattern which extends in a straight line in a positional direction, (b) a lattice pattern in which a line of the line pattern is sectioned at a constant interval, (c) a grid pattern in which the line of the line pattern is sectioned at an inconstant interval unlike the lattice pattern, (e) a bridge pattern in which the line pattern is partially connected to an adjacent line, (e) a hole pattern in which a hole is formed, and (f) a pillar pattern in which a pillar is formed.

In addition, there is a grid pattern in which a line is sectioned not at an equal interval in the lattice pattern but at a constant interval, a bridge pattern in which lines are connected to each other at a constant interval, a bridge pattern in which a line is cut in some places, or the like. The present invention is applicable to all of the above-described patterns. Further, targets to which the present invention is applicable are not limited to the above-described patterns. In other words, the present invention is not limited thereto a pattern created through the above-described SAxP, and is applicable to a pattern as long as the pattern is created according to a technique of creating a circuit pattern on the basis of a sidewall.

FIG. 5 is a diagram illustrating a layout of another circuit pattern which is created. As illustrated in FIG. 5, the present invention is also applicable to a pattern in which lines of the circuit pattern have different thicknesses. In addition, FIG. 4 illustrates the patterns in which lines vertically extend, but a direction of the circuit pattern changes depending on an imaging direction, and thus a direction of the circuit pattern is not limited to the direction illustrated in FIG. 4.

FIG. 6 illustrates examples of reference data, an inspection image, and a deformation of the inspection image. FIG. 6 illustrates an example of a grid pattern created through the SAxP. As design data for creating a circuit pattern, a reference data example 601 is used. In this case, an image obtained when the circuit pattern is imaged by the SEM is as in an ideal inspection image example (b). The ideal inspection image example (b) shows a circuit pattern part 602a, a white band 602b as an edge part thereof, and a base part 602c.

On the other hand, the circuit pattern created through the SAxP is as in a deformed inspection image example (c). As illustrated in FIG. 6(c), circuit pattern shift 603 occurs in the circuit pattern created through the SAxP. This can be notably seen from an overlay image (d) of the reference data and the deformed inspection image. Circuit pattern parts 604 and 606 match the reference data, but circuit pattern parts 605 and 607 are shifted to the right side.

FIG. 7 is an enlarged view of FIG. 6. There is a deformation rule according to a manufacturing method in a deformation amount of a line, and thus a shift occurs in an equal deformation amount at a constant cycle. In the SAxP, a circuit pattern created at a correct position and a shifted circuit pattern (a deviated circuit pattern) are mixed and created in a constant rule. This is a deformation of the SAxP. If there is such a deformation, the following problems occur, for example, in a case where the evaluation unit 106 performs comparison with reference data and evaluation. For example, even in a case where there is no problem (that is, no defect) including electrical characteristics, a defect may be evaluated due to a circuit pattern shift. In addition, the evaluation unit 106 may measure a length of a circuit pattern so as to perform evaluation. In this case, when a dimension is measured, the dimension may not be accurately measured since another edge enters a portion whose dimension is measured.

Therefore, the present invention provides a technique in which the deformation rule of the SAxP as an example is modeled as a shape deformation model, and reference data is deformed by using a deformation amount which is obtained according to the shape deformation model.

FIG. 8 illustrates an example of manufacturing steps of a circuit pattern using the SADP. FIG. 8 illustrates wafer sectional views. In addition, FIG. 9 illustrates a relationship between a width of a line part and a width of a space part of a circuit pattern created through the SADP. In the SADP, first, a resist pattern 801 which is formed through exposure is used as a sidewall, and film formation (deposition) is performed. During this step, a step such as slimming of the sidewall through etching may be performed.

Next, a step Spacer Etch is executed in which etching (spacer etch) is performed on a coating film 802 (a silicon oxide film in FIG. 8) which is formed so as to cover the resist pattern 801, and thus a thin film part 803 is removed. Consequently, only a thick film part 804 which is formed on a side surface of the resist pattern remains. Etching (HMetch) is performed by using the remaining thick film part 804 as a mask, and thus only a wiring part 805 is formed on the wafer. Here, "HM" stands for a hard mask.

In the SADP, since the resist pattern 801 is created which has a dimension larger than a dimension of a circuit pattern which is desired to be created, the resist pattern 801 is easily created. Therefore, a variation in a shape of the created resist pattern 801 or a shape of the slimmed resist pattern 806 is smaller than that of a circuit pattern which is desired to be created, and is stable. For this reason, as illustrated in FIG. 9, a difference between widths 901 and 902 of the resist patterns 801 which are formed through exposure, and a difference between widths 903 and 904 of the slimmed resist patterns 806 are smaller than the variation in the shape of the circuit pattern which is desired to be created.

In addition, it is possible to easily reduce variations in widths of the thick film parts 905, 906, 907 and 908 which are created through the deposition and the step Spacer Etch.

However, variations occur in a width 909 between the thick film part 905 and the thick film part 906 and a width 910 between the thick film part 906 and the thick film part 907 which are created through the step Spacer Etch.

FIG. 10 illustrates a case where a circuit pattern having consecutive lines is created through the SADP. In the SADP, if the resist pattern 801 and the thin film part 803 of the coating film 802 are removed through etching, widths 1001a and 1001b of portions where the resist patterns 801 were present are substantially the same as each other, and a width 1002a between thick film parts 1003b and 1003c generated between the resist patterns are substantially the same as a width 1002b between thick film parts 1003d and 1003e generated between the resist patterns. In other words, it is assumed that $1001a \cong 1001b$ and $1002a \cong 1002b$. In addition, the widths of the thick film parts 1003a to 1003e are also substantially the same as each other. In other words, it is assumed that $1003a \cong 1003b \cong 1003c \cong 1003d \cong 1003e$.

Therefore, in a case where such a circuit pattern is imaged by using the SEM, the circuit pattern appears that a line part is shifted in the same direction every other line as in a SEM image 1004.

Thus, in the present invention, a deformation in the SADP is modeled by using the above-described assumption. Since it is assumed that $1003a \cong 1003b \cong 1003c \cong 1003d \cong 1003e$, a portion where there is no variation in line width is used as a line part 1005 of the circuit pattern. In addition, in the deformation of the circuit pattern, it is assumed that the lines of the circuit pattern are shifted in the horizontal direction every other line by $1001a - 1002a$ ($\cong 1001b - 1002b$), and thus a space part 1006 is deformed.

However, in an inspection image, there is a case where a line width or a space width of a circuit pattern may be varied by factors other than the SADP due to a deformation during manufacturing, noise, or an imaging error. Therefore, when the line part 1005 of the circuit pattern is determined, a distance between edges may be compared every other set, and a portion with a smaller variation may be used as the line part 1005. In addition, in relation to the space part 1006, a distance between edges may be compared every other set, and a portion with a greater variation may be used as the space part 1006. The variation can be obtained by computing a standard deviation or a variance of a set of edge widths. Further, in a case of the SADP, a width of the space part is divided into two types of widths, one type of width of the space part is excluded, then a variation in the other type of width of the space part is obtained, and if the variation is smaller than a variation obtained in widths of all the space parts, it can be determined that there is a possibility of the SADP.

FIG. 11 illustrates an example of manufacturing steps of a circuit pattern using the SATP. FIG. 11 illustrates wafer sectional views. A step Deposition 1 illustrated in FIG. 11 shows a part of the step $SiO_2$ depo showing the consecutive line patterns in FIG. 10. Manufacturing steps are the same as the steps up to film formation (step Deposition 1) in the SADP.

Removal 1 of the film formed in the step Deposition 1 is performed, and thus only the thin film part 803 of the coating film 802 is removed. If film formation 2 (Deposition 2) is performed by using the resist pattern 801 and the thick film part 804 formed through the film removal 1 as sidewalls, a coated film 1101 is formed.

Next, removal (film removal 2) of the coated film 1101 formed in the step Deposition 2 is performed again so that a thin film part 1102 is removed, and only a thick film part 1103 of the coated film 1101 remains. Next, a step Spacer Etch is executed on the resist pattern 801, the thick film part 804, and the thick film part 1103 created through the film removal 2 so that only the thick film part 804 is removed.

A step HM Etch is performed by using remaining resist patterns 801a and 801b and thick film parts 1103a, 1103b, 1103c and 1103d as a hard mask, and thus a gate 1106 is created by using the SATP. A width of the gate 1106 created at this time is determined depending on the resist patterns 801a and 801b and the thick film parts 1103a, 1103b, 1103c and 1103d.

In addition, a width of a space 1107 between the gates 1106 is determined depending on the thick film part 804, and the thin film part 1102 interposed between the thick film parts 1103. For this reason, a width of the line part in the SATP may be divided into two types of widths including line part widths 801a and 801b created by the resist patterns 801, and line part widths 1103a, 1103b, 1103c and 1103d created by the thick film parts 1103.

A width of a space part in the SATP may be divided into two types of widths including space widths 1105a, 1105b, 1105c and 1105d created by the thick film parts 804, and space widths 1104a, 1104b and 1104c created by the thin film parts 1102. In FIG. 11, a repeated circuit pattern is assumed, and thus the same circuit pattern is assumed to be also repeated outside (that is, outside FIG. 11) space widths 1104a and 1104c in the step Space Etch. In FIG. 11, the space widths 1104a and 1104c are defined on the basis of this assumption, but the present invention is not limited to a repeated circuit pattern.

The SATP is modeled. First, in the same manner as in the SADP, it is assumed that $801a \cong 801b$, and $1003a \cong 1003b \cong 1003c \cong 1003d$. In addition, it is assumed that $1104a \cong 1104b \cong 1104c$, and $1105a \cong 1105b \cong 1105c \cong 1105d$.

In this case, in the SATP model, with 1103b as a reference of determination, $W_1 = |801a - 1103b|$, $W_2 = |1103c - 1103b|$, and $W_3 = |1103a - 1103b|$ (or $W_4 = |1103c - 801b|$) are computed. Here, $(W_2 \cong W_3) < W_1$ is established. In addition, if $W_4$ is used, this leads to $W_2 < (W_1 \cong W_4)$. This expression is a model of the SATP.

In addition, with 1105c as a reference of determination, $W_1' = |1104b - 1105c|$, $W_2' = |1105c - 1105b|$, and $W_3' = |1105d - 1104c|$ (or $W_4' = |1105b - 1105c|$) are computed. Here, $W_2' < (W_1' \cong W_3')$ is established. Further, if $W_4'$ is used, this leads to $(W_2' \cong W_4') < W_1'$. This expression is also a model of the SATP. A reference of determination is not limited thereto. Still further, widths used to compute $W_1$, $W_2$, $W_3$, and $W_4$, and $W_1'$, $W_2'$, $W_3'$, and $W_4'$ are changed depending on line widths or space widths, and thus are not limited to the above-described content. If it is checked whether or not the model is applicable by using all widths between edges as references, accuracy of model estimation is improved. As described above, if the model is applicable, it can be determined that there is a possibility of the SATP.

FIG. 12 illustrates an example of manufacturing steps of a circuit pattern using the SAQP. FIG. 12 illustrates wafer sectional views. A step Spacer Etch 1 illustrated in FIG. 12 shows a part of the step Spacer Etch showing the consecutive line patterns in FIG. 10. Manufacturing steps are the same as the steps up to the step of removing the resist pattern 801 and the coating film 802 through the etching (the step Spacer Etch 1) in the SADP.

Film formation (step Deposition 2) is performed again by using the thick film part 804 which is formed in the step Spacer Etch 1 as a sidewall, so as to create a coating film 1201. The created coating film 1201 is removed so that only a thick film part 1202 and the thick film part 804 remain.

Next, etching (step Spacer Etch 2) is performed so that the sidewall formed by the thick film part 804 is removed. A step HM Etch is performed by using a remaining thick film part 1203 as a hard mask, and thus a gate 1204 is created by using the SAQP.

In this case, the thick film part 1203 has a smaller variation than the space part because of film thickness accuracy of the formed film. Thus, it is considered that the gate 1204, that is, a line part has a constant width. On the other hand, a space part between the gates 1204 may be divided into three types of space parts including space parts 1205 (1205*a*, 1205*b*, 1205*c*, and 1205*d*) which are determined depending on widths of the thick film parts 804 of the coating films 802 illustrated in FIG. 8, space parts 1206 (1206*a* and 1206*b*) which are determined depending on values obtained by subtracting widths of the thick film parts 1203 from the widths of the resist patterns 801, and space parts 1207 (1207*a*, 1207*b*, and 1207*c*) which are determined depending on values obtained by subtracting the widths of the thick film parts 1203 from spaces between the thick film parts 804 in portions where the resist patterns 801 are not present.

The SAQP is modeled. First, since the gates 1204 (that is, the line parts) have small variations, a variance or a standard deviation of widths between edges is obtained every other line, and a line having the smaller variance or standard deviation can be determined as a line part. This is the same as in the SADP.

In the SAQP, it may be assumed that the space parts 1205*a*≅1205*b*≅1205*c*≅1205*d*, and the space parts 1206*a*≅1206*b*, and the space parts 1207*a*≅1207*b*≅1207*c*. Therefore, in a case where variations in the space parts are observed in a state of excluding one type of the space part, the variations are small in the set of space parts 1205 (1205*a*, 1205*b*, 1205*c*, and 1205*d*), and the variations are great in the mixed set of the space parts 1207 and 1206. The variations can be compared with each other by using a standard deviation or a variance. This is a model of the SAQP.

In addition, in the SAQP, determination can also be performed by comparing differences between widths of the space parts with each other. For example, when the space part is used as a reference, space parts which are adjacent to each other with a line part interposed therebetween may satisfy |1205*a*-1205*b*|<|1206*a*-1207*b*|. If this relational expression is satisfied, the SAQP may be determined. A relational expression of a difference between the space parts is not limited to the above-described expression. If it is checked whether or not the model is applicable by using all widths between edges as references, accuracy is improved.

Next, a description will be made of a process performed by the model estimation unit 103 illustrated in FIG. 1. Hereinafter, the model estimation unit 103 will be described, but the same process is performed by the model estimation unit 201 illustrated in FIG. 2. FIG. 13 is a diagram illustrating a configuration of the model estimation unit 103 and a process flow. The model estimation unit 103 includes a vertical (horizontal) direction luminance profile calculation portion 1301, an edge position computation portion 1302, an inter-edge width computation portion 1303, and a model determination portion 1304.

The vertical (horizontal) direction luminance profile calculation portion 1301 computes a luminance profile so as to create a luminance profile of at least one of a vertical direction and a horizontal direction of an inspection image. In the following example, a line direction of a pattern is assumed as the vertical direction. In addition, if a line direction of the pattern is the horizontal direction, a horizontal direction profile is created. For example, in a case where reference data is input as in the model estimation unit 201 illustrated in FIG. 2, as a profile acquisition direction, a profile only in a line direction may be obtained by analyzing the reference data. In the analysis of the reference data, a line direction can be determined by using, for example, Hough conversion. Further, information regarding a line direction may also be included as additional information of reference data.

In a case where reference data is not input, a profile acquisition direction can be obtained by extracting an edge from an inspection image and by using Hough conversion. The edge extraction may be performed by using a general edge extracting filter such as a Sobel filter or a Laplacian filter. A method of determining a line direction or a filter is not limited thereto.

FIG. 14 illustrates a luminance profile created for a SEM image (inspection image) 1401 of a line pattern. The luminance profile illustrated in FIG. 14 is obtained by plotting an accumulated value of luminance values in the Y direction (that is, an added value of luminance values in the Y direction) on an axis in the X direction. In the SEM image 1401, an edge part 1402 of a circuit pattern is shown as a white band, and thus widths of a line part and a space part can be obtained only by taking a profile in one direction. In a case where there is no feature such as the white band, a contour line may be extracted, and a profile may be obtained from the extracted contour line. A profile may be computed by using four arithmetic operations of luminance values. The vertical (horizontal) direction luminance profile calculation portion 1301 outputs the created luminance profile to the edge position computation portion 1302.

The edge position computation portion 1302 computes an edge position on the basis of the luminance profile. As illustrated in FIG. 14, for example, in a case where an added value of the luminance values is used, a local peak position 1403 of the profile is an edge position. In addition, in a case where a luminance profile is created on the basis of an inspection image or an image as a result of performing smoothing or contour line extraction on the inspection image, a luminance profile may be influenced by noise. As a countermeasure for this, a noise removal process such as a smoothing process may be performed on an acquired luminance profile.

In addition, a peak acquired from a luminance profile may be, for example, a value which is equal to or greater than a predetermined threshold value (for example, a value of 50% of the maximum value) of the profile after the profile is smoothened. In addition, in a case where reference data is input, the number of edges in a profile acquisition direction can be acquired on the basis of a visual field range of an inspection image for the reference data, and thus peaks corresponding to the edges may be obtained. Information regarding the number of edges may be acquired when the reference data is analyzed by the vertical (horizontal) direction luminance profile calculation portion 1301, and may be acquired when the inter-edge width computation portion 1303 may perform the same analysis. In addition, the information regarding the number of edges may be given in advance as additional information of the reference data. Further, a method of acquiring a peak is not limited thereto.

The inter-edge width computation portion 1303 computes a width between the edge positions acquired by the edge position computation portion 1302. Here, a width between adjacent edges is obtained. The width between edges may be obtained by computing a distance between peaks, and may be obtained on the basis of values of the vicinities of the peaks in the units of sub-pixels. For example, a method of obtaining a peak of a differential value of a profile may be used to compute a sub-pixel. The inter-edge width computation portion 1303 outputs the calculated width between edges to the model determination portion 1304.

The model determination portion 1304 performs a model estimation process by using the width between edges calculated by the inter-edge width computation portion 1303. Specifically, the model determination portion 1304 determines whether the calculated width between edges corresponds to a line part or a space part of the circuit pattern, and estimates a shape deformation model by using a relational expression (that is, the above-described relation expressions of the SADP, the SATP, and the SAQP) representing a relation of a width of the line part and the space part of the circuit pattern in the inspection image. FIG. 15 illustrates an example in which a peak is calculated from a luminance profile, and a width between adjacent peaks is calculated as a width between edges.

For example, in a case where of the SADP, variances are obtained by using both a set of widths between edges such as inter-edge widths 1501*a*, 1501*b*, 1501*c*, 1501*d*, and 1501*e* illustrated in FIG. 15 and a set of widths between edges such as inter-edge widths 1502*a*, 1502*b*, 1502*c*, and 1502*d*. A portion having a smaller variance of the obtained variances is determined as a line part.

In addition, in a case where |1502*a*-1502*c*|≅|1502*b*-1502*d*|<|1502*a*-1502*b*|≅|1502*c*-1502*d*| is satisfied, it can be determined that there is a possibility of the SADP. The model determination portion 1304 determines whether or not all the above-described models of the SADP, the SATP and the SAQP match the corresponding relational expressions. In addition, the model determination portion 1304 determines a plausible model as a manufacturing model. For example, a method is used in which a model which most matches the relational expressions is employed as the manufacturing model. In addition, model determination may be performed by using all distances between edges, and thus accuracy of the model determination is further improved.

There is a case where it is determined that the calculated widths between edges are all the same as each other, that is, a line part and a space part are arranged at equal intervals, and thus a model cannot be determined. In this case, as an exceptional process, an appropriate model is applied, or the subsequent deformation process is not performed. In a case where an appropriate model is applied, it is preferable to use the SAQP model having a large deformation variation in a space width. In addition, in a case where reference data is input, there is a difference in a line width or a space width of the reference data, a model can be estimated through comparison with the reference data. Determination of a model is not limited to this method. Further, a model can also be estimated for a pattern which is created according to a method in which a manufacturing step is replaced or a method in which manufacturing steps are combined with each other, such as replacing the step "film removal (FIG. 12)" of the SAQP with the step "film removal 1 (FIG. 11)" of the SATP.

Information regarding a manufacturing model may be input to the model estimation unit 103. In this case, as illustrated in FIG. 3, the model estimation unit 103 illustrated in FIG. 1 may be omitted. However, in a case where a process in the model estimation unit 103 is omitted, processes performed by the vertical (horizontal) direction luminance profile calculation portion 1301, the edge position computation portion 1302, and the inter-edge width computation portion 1303 are required to be performed by the deformation amount estimation unit 301.

FIG. 16 is a diagram illustrating a configuration of the deformation amount estimation unit 104 and a process flow. Hereinafter, although the deformation amount estimation unit 104 is described, the same process can also be performed by the deformation amount estimation unit 202 illustrated in FIG. 2 or the deformation amount estimation unit 301 illustrated in FIG. 3.

The deformation amount estimation unit 104 includes a deformation reference determination portion 1601 and a deformation amount calculation portion 1602. The model and the widths between edges obtained by the model estimation unit 103 are input to the deformation amount estimation unit 104. The widths between edges may be calculated in the deformation amount estimation unit 104 again. In the following description, even in a case where a model is included in reference data, the model estimation unit 103 calculates widths between edges or the like.

The deformation reference determination portion 1601 determines a reference edge of an inspection image. The reference edge is an edge which is used as a reference of deformation (shift). As the reference edge, an edge which is not deformed (shifted) may be selected. FIG. 17 illustrates an example of a method of determining the reference edge. As the reference edge, for example, as illustrated in FIG. 17, an edge which is closest to a central line of an inspection image may be selected. A method of determining the reference edge is not limited thereto. In addition, the reference edge may be determined in the same manner for other circuit patterns such as in a circuit in which a lattice pattern, a hole, or the like is formed in a vertical direction, and a circuit pattern is created in a horizontal direction through a combination of the SADP, the SATP, and the SAQP.

The deformation amount calculation portion 1602 obtains a deformation amount relative to the reference edge which is determined by the deformation reference determination portion 1601. Specifically, the deformation amount calculation portion 1602 obtains a deformation amount of the inspection image according to a constraint condition which defines a cyclic relationship between a width of a line part and a width of a space part of a circuit pattern of the estimated shape deformation model.

FIG. 18 illustrates an example of a method of estimating a deformation amount. FIG. 18(*a*) is a diagram illustrating a luminance profile created for the inspection image of a line pattern, and FIG. 18(*b*) is a diagram illustrating reference data.

In the SADP, the space parts around the reference edge have cyclic deformation every two space parts, and thus two widths (X1 and X2) are obtained as a width X of the space part as illustrated in FIG. 18(*a*). Here, a width TL up to the vicinity edges of the line parts over the cycle is referred to as a "cyclic length". In the example illustrated in FIG. 18(*a*), TL=LL+X1+X2 is given as the constraint condition from a relationship between a line part width LL and the cyclic length TL.

Regarding calculation of X1 and X2, if TL and LL are respectively obtained on the basis of, for example, average values of edge widths, reference values of X1 and X2 may also be obtained on the basis of average values of edge widths, and thus TL−LL=X1+X2+α is given. Here, it is assumed that X1A and X2A are averages of edge widths as references of X, and α is an error caused by the averages. Therefore, X1 and X2 can be respectively obtained from equations, that is, X1=X1A+α/2 and X2=X2A+α/2. A method of computing the widths X1 and X2 of the space parts is not limited thereto.

In the SATP, as a width of a space part, two types of widths are obtained for three space parts. In addition, in the SATP, six types of combinations of lengths between edges are obtained. Since a cyclic length in the SATP extends over two line parts, when the cyclic length is denoted by TL, and two line widths are respectively denoted by L1 and L2, an equation, that is, TL−L1−L2=X1+2X2+α, or TL−2L1=X1+2X2+α is given. Here, L1 indicates an average of widths of line parts corresponding to 1103 illustrated in FIG. 11, and L2 indicates an average of widths of line parts corresponding to 801 illustrated in FIG. 11. X1 indicates a width of a space part corresponding to 1104 illustrated in FIG. 11, and X2 indicates a width of a space part corresponding to 1105 illustrated in FIG. 11. Which one of the two equations is used may be determined depending on a reference edge. Averages of edge widths may be used to compute X1 and X2 in the same manner as in the SADP. A method of computing the widths X1 and X2 of the space parts is not limited thereto.

In addition, in the SAQP, as a width of a space part, three types of widths are obtained for three space parts. Further, in the SAQP, two types of combinations of lengths between edges are obtained. When a cyclic length is denoted by TL, and an average of line part widths is denoted by L, a constraint condition of the widths X1, X2 and X3 of the space parts is TL−3L=X1+X2+X3+α. Averages of edge widths may be used to compute X1, X2, and X3 in the same manner as in the SADP. A method of computing the widths of the space parts is not limited thereto.

In a width of a space part, an edge width to be referred to differs depending on which edge of the circuit pattern corresponds to a reference edge. As a line part and a space part of a circuit pattern become more uniform, it is more difficult to determine the line part and the space part on the basis of variations. Therefore, for example, two types of widths may be obtained as in cases where, in a vertical line pattern created through the SADP, a reference edge is set to a right edge and a left edge of the line pattern, and, in evaluation of the pattern, reference data may be deformed for each of the obtained types of widths of space parts so that deformed reference data is created so as to correspond to the number of types of widths of space parts.

FIG. 19 is a diagram illustrating a configuration of the reference data deformation unit 105 and a process flow. The reference data deformation unit 105 includes a deformation reference determination portion 1901 and a deformation processing portion 1902.

The deformation reference determination portion 1901 determines a reference edge in reference data. As the reference edge, for example, an edge which is closest to a central coordinate of the reference data may be selected in the same manner as in the deformation reference determination portion 1601. A method of selecting the reference edge is not limited thereto. In addition, as in FIG. 5, in a characteristic case such as a case where lines have a plurality of widths due to design data, the lines can be aligned through comparison with an edge width of an inspection image, and a deformation reference can be more easily determined.

The deformation processing portion 1902 performs a deformation process centering on the reference edge. For example, in reference data of a line pattern, a line part including the reference edge may be fixed, and vicinity edges of the line part may be shifted to either of the left side and the right side so as to match a width of a space part obtained by the deformation amount estimation unit 104. When the edges are shifted, a width of the line part of the reference data is not changed.

In addition, an actual shift amount may be obtained, for example, by using the space width of the reference data illustrated in FIG. 18(*b*). For example, the actual shift amount may be obtained by using a difference between a width $X1_0$ of the space part of the reference data and the space part X1 of the inspection image, a difference between a width $X2_0$ of the space part of the reference data and the space part X2 of the inspection image, or the like.

In addition, there is a case where there may be deformation in a line part of an inspection image, such as thinning or thickening, and thus a deformation amount (that is, a width of a space part) does not match reference data. For example, in a case of the SADP, a distance between lines observed in a state in which one line part is excluded in an inspection image may be smaller than a distance which matches widths of two types of space parts and a width of the line part.

In this case, the deformation processing portion 1902 computes a width of a space part again by using the constraint condition of a deformation amount and the reference data mentioned in the description of the deformation amount calculation portion 1602. For example, with reference to FIG. 18, readjustment of a width of a space part in the SADP will be described. A cyclic length in reference data is denoted by $TL_0$, and a width of a line part in the reference data is denoted by $LL_0$ (refer to FIG. 18(*b*)). If $TL_0$=X1+X2+$LL_0$ is not satisfied, $TL_0$−(X1+X2+$LL_0$)=β is computed. In addition, actual widths of space parts may be set to X1'=X1−β/2, X2'=X2−β/2, and the like. Also in the SATP and the SAQP, a width of a space part may be adjusted according to the constraint condition mentioned in the description of the deformation amount calculation portion 1602. Further, the above-described readjustment is only an example, and different computation expressions may be used in cases where a line part is thin and thick.

Further, in a case where reference data is given to the deformation amount estimation unit 104 as an input from the reference data storage unit 102, the above-described adjustment may be performed by the deformation amount estimation unit 104. Still further, information for identifying a line part and a space part is added to the reference data, a corresponding width of a width of a line part and a width of a space part obtained by the deformation amount estimation unit 104 may be used. Furthermore, in a case where a line part and a space part are specified from an inspection image by a pattern created through the SADP or the SAQP, a width of the line part or a width of the space part can be further more easily selected. Moreover, the reference data deformation unit 105 outputs the deformed reference data which has been deformed to the evaluation unit 106.

The evaluation unit 106 receives the deformed reference data which has been deformed by the reference data deformation unit 105 and an inspection image, and performs an evaluation process. The content of the evaluation process includes, for example, shape evaluation through comparison between contour lines of patterns, a length measurement process for measuring a pattern dimension, and pattern matching for specifying a visual field deviation in the inspection image. A process in the evaluation unit 106 is not limited to the above-described content or evaluation methods of the related art. In addition, the evaluation unit 106 stores a final evaluation result in the evaluation result storage unit 107.

Further, among the layouts of the circuit patterns illustrated in FIG. 4, a pattern may be created by using the SAxP both in the vertical direction and in the horizontal direction except for the line pattern (a). In this case, the present invention is applied to both the vertical direction and the horizontal direction so that a deformation amount of a width or the like of a space part can be obtained.

According to the pattern evaluation device 100 of the present embodiment, shape deformation caused by a manufacturing step is modeled in advance for each manufacturing step (SAxP), a shape deformation model is estimated from an inspection image, and a deformation amount is estimated on the basis of a constraint condition of the estimated shape deformation model. In addition, the pattern evaluation device 100 deforms reference data (design data) on the basis of the estimated deformation amount, and performs evaluation by using the deformed reference data and the inspection image. In the above-described model, for example, line parts or space parts of a circuit pattern, which have substantially the same width through a manufacturing step are collected as a set, and a deformation amount is determined according to a constraint condition in which all deformation amounts of the pattern corresponding to the reference data are the same as each other in the set. Consequently, it is possible to perform evaluation by taking into consideration only shape deformation caused by a design layout. Therefore, reliability of the pattern evaluation is improved.

The pattern evaluation device of the present invention may be mounted in a visual inspection device (for example, a scanning electron microscope (SEM)) as illustrated in FIG. 20. FIG. 20 is a diagram illustrating a configuration of a scanning electron microscope. For example, the pattern evaluation device may be mounted in a controller 2514.

The scanning electron microscope includes an optical system which scans and irradiates a sample surface with an electron beam, and a detection system which forms an inspection image by detecting a secondary electron from the sample. In the scanning electron microscope, an electron beam 2503 is extracted by an extraction electrode 2502 from an electron source 2501, and is accelerated by an acceleration electrode (not illustrated). The accelerated electron beam 2503 is narrowed by a condenser lens 2504 which is an aspect of a focusing lens, and a sample 2509 is one-dimensionally or two-dimensionally scanned with the electron beam by a scanning deflector 2505.

The electron beam 2503 is decelerated by a negative voltage which is applied to an electrode built into a sample stage 2508, and is focused by lens action of an objective lens 2506 so as to be applied to the sample 2509. If the sample 2509 is irradiated with the electron beam 2503, electrons 2510 such as a secondary electron and a backscattering electron are emitted from the irradiation location. The emitted electrons 2510 are accelerated in a direction of the electron source by acceleration action based on the negative voltage applied to the sample 2509 so as to collide with a conversion electrode 2512 and to generate a secondary electron 2511.

The secondary electron 2511 emitted from the conversion electrode 2512 is captured by a detector 2513, and an output I of the detector 2513 changes depending on an amount of captured secondary electrons. A luminance of a display device (not illustrated) changes according to the output I. For example, in a case where a two-dimensional image is formed, a deflection signal input to the scanning deflector 2505 is synchronized with the output I of the detector 2513, and thus an image of a scanning region is formed. In addition, the scanning electron microscope exemplified in FIG. 20 includes a deflector (not illustrated) which moves a scanning region of the electron beam 2503.

The controller 2514 controls each constituent element of the scanning electron microscope and also forms an image on the basis of a detected electron. In addition, the controller 2514 has a function of measuring a width of a pattern formed on the sample 2509 on the basis of an intensity distribution of a detected electron, called a line profile.

FIG. 21 is a diagram illustrating a configuration of the controller 2514. The controller 2514 is an information processing device such as a general purpose computer. The controller 2514 includes a CPU 2101, an image memory 2102, an LSI 2103, an output device 2104, and a storage device 2105. In addition, the controller 2514 is connected to a design system 2108 and a controller 2107 of the design system 2108 via a network such as a LAN. Therefore, the controller 2514 can acquire reference data such as design data via the network. Consequently, the pattern evaluation device of the controller 2514 can evaluate performance of an inspection image by comparing the reference data such as design data from the design system 2108 with the inspection image captured by the scanning electron microscope.

In addition, the present invention is not limited to the above-described embodiments, and includes various modification examples. For example, the above-described embodiments have been described in detail for better understanding of the present invention, but are not limited to including all the above-described constituent elements. In addition, some constituent elements of a certain embodiment may be replaced with constituent elements of another embodiment, and a configuration of a certain embodiment may be added to a configuration of another embodiment. Further, some constituent elements of each embodiment may be added to, deleted, or replaced with other constituent elements.

As described above, some or all of the constituent elements of the embodiments may be realized by hardware, for example, by designing the constituent elements with integrated circuits. In addition, the present invention may be realized by program codes of software for realizing the functions of the embodiments. In this case, a recording medium which records the program codes is provided to an information processing device, and the information processing device (or a CPU) reads the program codes stored on the recording medium. In this case, the program codes read from the recording medium realize the functions of the above-described embodiments, and thus the program codes and the recording medium storing the program codes configure the present invention. As recording media for supplying the program codes, for example, a flexible disc, a CD-ROM, a DVD-ROM, a hard disk, an optical disc, a magneto-optical disc, a CD-R, a magnetic tape, a nonvolatile memory card, and a ROM are used.

In addition, the program codes of the software for realizing the functions of the embodiments may be transmitted via a network and may be stored in a storage device of an information processing device or a storage medium such as a CD-RW or a CD-R, and a CPU of the information processing device may read the program codes stored in the storage device or the storage medium and may execute the program codes.

It can be understood by a person skilled in the art that there are a plurality of combinations of hardware, software, and firmware suitable for implementing the present invention. For example, the program codes for realizing the functions of the embodiments may be mounted with various programs or script languages such as an assembler, C/C++, perl, Shell, PHP, and Java (registered trademark).

In addition, the illustrated control lines or information lines in the drawings are considered to be necessary for description, and thus it cannot necessarily be said that all control lines or information lines in a product are illustrated. All constituent elements may be connected to each other.

REFERENCE SIGNS LIST

100: pattern evaluation device
101: inspection image storage unit
102: reference data storage unit
103: model estimation unit
104: deformation amount estimation unit
105: reference data deformation unit
106: evaluation unit
107: evaluation result storage unit
200: pattern evaluation device
201: model estimation unit
202: deformation amount estimation unit
300: pattern evaluation device
301: deformation amount estimation unit
1301: direction luminance profile calculation portion
1302: edge position computation portion
1303: inter-edge width computation portion
1304: model determination portion
1601: deformation reference determination portion
1602: deformation amount calculation portion
1901: deformation reference determination portion
1902: deformation processing portion
2101: CPU
2102: image memory
2103: LSI
2104: output device
2105: storage device
2107: controller
2108: design system
2501: electron source
2502: extraction electrode
2503: electron beam
2504: condenser lens
2505: scanning deflector
2506: objective lens
2508: sample stage
2509: sample
2510: electron
2511: secondary electron
2512: conversion electrode
2513: detector
2514: controller

The invention claimed is:

1. A pattern evaluation device which evaluates a pattern included in an inspection image by using reference data, the device comprising:
a model estimation unit that estimates a shape deformation model caused by a periodic positional deviation of the pattern generated in a process of manufacturing the pattern on the basis of the inspection image prior to deformation of the inspection image;
wherein the model estimation unit estimates the shape deformation model by determining whether a comparison result obtained based on a comparison of dimensions between different edge-to-edge positions matches the shape deformation model set for each of a plurality of manufacturing methods of patterns;
a deformation amount estimation unit that estimates a deformation amount of the inspection image based on a constraint condition of the estimated shape deformation model;
a reference data deformation unit that deforms the reference data by using the estimated deformation amount; and
an evaluation unit that performs an evaluation process by comparing the reference data which is deformed by the reference data deformation unit with the inspection image;
wherein pattern parts and space parts of the pattern having substantially a same width are arranged in a set, and the deformation amount is determined based on the constraint condition such that deformation amounts of the pattern parts and the space parts have a same value in the set; and
wherein the constraint condition defines a cyclic relationship between a width of the pattern parts and a width of the space parts of the pattern of the estimated shape deformation model as $TL-2L1=X1+2X2+\alpha$, where TL is a cyclic length, L1 is an average of widths of pattern parts, X1 and X2 are widths of space parts, and $\alpha$ is an error value.

2. The pattern evaluation device according to claim 1, wherein the shape deformation model is obtained by modeling a deformation rule according to a manufacturing method in which a circuit pattern is manufactured on the basis of a sidewall.

3. The pattern evaluation device according to claim 1, wherein the shape deformation model is obtained by modeling a deformation rule for self-aligned triple patterning (SATP).

4. The pattern evaluation device according to claim 1, wherein the model determination portion determines whether a calculated inter-edge width corresponds to a pattern part or a space part of a circuit pattern, and determines the shape deformation model by using a relational expression representing a relationship between a width of the pattern part and a width of the space part.

5. The pattern evaluation device according to claim 4, wherein the model determination portion determines whether or not the calculated inter-edge width corresponds to a pattern part or a space part by using a value indicating a variation in the calculated inter-edge width.

6. The pattern evaluation device according to claim 1, wherein the reference data deformation unit computes the deformation amount again by using the constraint condition and the reference data.

7. The pattern evaluation device according to claim 1, wherein the model estimation unit estimates the shape deformation model by using the reference data.

8. The pattern evaluation device according to claim 1, wherein the deformation amount estimation unit estimates a deformation amount of the inspection image by using the reference data.

9. A pattern evaluation device which evaluates performance of a pattern included in an inspection image by using reference data, the device comprising:
a storage device that stores reference data including information regarding a shape deformation model caused by a manufacturing method, wherein the shape deformation model is estimated and stored in advance, prior to deformation of the inspection image, by using a relational expression representing a relationship between a width of a pattern part and a width of a space part of a circuit pattern in the inspection image;
a deformation amount estimation unit that estimates a deformation amount of the inspection image by using the reference data;
a reference data deformation unit that deforms the reference data by using the estimated deformation amount; and
an evaluation unit that performs an evaluation process by comparing the reference data which is deformed by the reference data deformation unit with the inspection image;
wherein pattern parts and space parts of the pattern having substantially a same width are arranged in a set, and the deformation amount is determined such that deformation amounts of the pattern parts and the space parts have a same value in the set; and
wherein the constraint condition defines a cyclic relationship between a width of the pattern parts and a width of the space parts of the pattern of the estimated shape deformation model as TL−2L1=X1+2X2+α, where TL is a cyclic length, L1 is an average of widths of pattern parts, X1 and X2 are widths of space parts, and α is an error value.

10. A visual inspection device comprising:
an optical system that scans and irradiates a sample surface with light or a charged particle;
a detection system that forms an inspection image by detecting an electron from the sample; and
the pattern evaluation device according to claim 1.

11. A pattern evaluation device which evaluates performance of a pattern included in an inspection image by using reference data, the device comprising:
a model estimation unit that estimates a shape deformation model caused by a manufacturing method on the basis of the inspection image prior to deformation of the inspection image;
wherein the model estimation unit estimates the shape deformation model by using a relational expression representing a relationship between a width of a pattern part and a width of a space part of a circuit pattern in the inspection image;
wherein the model estimation unit includes
a luminance profile calculation portion that creates a luminance profile of the inspection image in at least one direction of a vertical direction and a horizontal direction;
an edge position computation portion that computes an edge position on the basis of the luminance profile;
an inter-edge width computation portion that computes a width between the edge positions; and
a model determination portion that determines the shape deformation model by using an inter-edge width calculated by the inter-edge width computation portion;
a deformation amount estimation unit that estimates a deformation amount of the inspection image based on a constraint condition of the estimated shape deformation model;
a reference data deformation unit that deforms the reference data by using the estimated deformation amount; and
an evaluation unit that performs an evaluation process by comparing the reference data which is deformed by the reference data deformation unit with the inspection image;
wherein pattern parts and space parts of the pattern having substantially a same width are arranged in a set, and the deformation amount is determined based on the constraint condition such that deformation amounts of the pattern parts and the space parts have a same value in the set; and
wherein the constraint condition defines a cyclic relationship between a width of the pattern parts and a width of the space parts of the pattern of the estimated shape deformation model as TL−2L1=X1+2X2+α, where TL is a cyclic length, L1 is an average of widths of pattern parts, X1 and X2 are widths of space parts, and α is an error value.

12. A pattern evaluation device which evaluates performance of a pattern included in an inspection image by using reference data, the device comprising:
a model estimation unit that estimates a shape deformation model caused by a manufacturing method on the basis of the inspection image prior to deformation of the inspection image;
wherein the model estimation unit estimates the shape deformation model by using a relational expression representing a relationship between a width of a pattern part and a width of a space part of a circuit pattern in the inspection image;
a deformation amount estimation unit that estimates a deformation amount of the inspection image based on a constraint condition of the estimated shape deformation model;
wherein the deformation amount estimation unit estimates a deformation amount of the inspection image according to a constraint condition which defines a cyclic relationship between the width of the pattern part and the width of the space part of the circuit pattern of the estimated shape deformation model;
a reference data deformation unit that deforms the reference data by using the estimated deformation amount; and
an evaluation unit that performs an evaluation process by comparing the reference data which is deformed by the reference data deformation unit with the inspection image;
wherein pattern parts and space parts of the pattern having substantially a same width are arranged in a set, and the deformation amount is determined based on the constraint condition such that deformation amounts of the pattern parts and the space parts have a same value in the set; and
wherein the constraint condition defines a cyclic relationship between a width of the pattern parts and a width of the space parts of the pattern of the estimated shape deformation model as TL−2L1=X1+2X2+α, where TL is a cyclic length, L1 is an average of widths of pattern parts, X1 and X2 are widths of space parts, and α is an error value.

13. A pattern evaluation device which evaluates performance of a pattern included in an inspection image by using reference data, the device comprising:
a storage device that stores reference data including information regarding a shape deformation model caused by a manufacturing method, wherein the shape deformation model is estimated and stored in advance, prior to deformation of the inspection image, by (i) creating a luminance profile of the inspection image in at least one of a vertical direction and a horizontal direction, (ii) computing a first edge position based on the luminance profile, (iii) computing a width between the first edge position and a second edge position, and (iv) determining the shape deformation model by using an inter-edge width calculated by an inter-edge width computation portion;

a deformation amount estimation unit that estimates a deformation amount of the inspection image by using the reference data;

a reference data deformation unit that deforms the reference data by using the estimated deformation amount; and an evaluation unit that performs an evaluation process by comparing the reference data which is deformed by the reference data deformation unit with the inspection image;

wherein pattern parts and space parts of the pattern having substantially a same width are arranged in a set, and the deformation amount is determined such that deformation amounts of the pattern parts and the space parts have a same value in the set; and wherein the constraint condition defines a cyclic relationship between a width of the pattern parts and a width of the space parts of the pattern of the estimated shape deformation model as $TL-2L1=X1+2X2+\alpha$, where TL is a cyclic length, L1 is an average of widths of pattern parts, X1 and X2 are widths of space parts, and $\alpha$ is an error value.

14. A pattern evaluation device which evaluates performance of a pattern included in an inspection image by using reference data, the device comprising:

a storage device that stores reference data including information regarding a shape deformation model caused by a manufacturing method prior to deformation of the inspection image;

a deformation amount estimation unit that estimates a deformation amount of the inspection image by using the reference data;

a reference data deformation unit that deforms the reference data by using the estimated deformation amount; and an evaluation unit that performs an evaluation process by comparing the reference data which is deformed by the reference data deformation unit with the inspection image, wherein the deformation amount estimation unit estimates a deformation amount of the inspection image according to a constraint condition which defines a cyclic relationship between a width of pattern parts and a width of space parts of a circuit pattern of the estimated shape deformation model as $TL-2L1=X1+2X2+\alpha$, where TL is a cyclic length, L1 is an average of widths of pattern parts, X1 and X2 are widths of space parts, and $\alpha$ is an error value; and wherein pattern parts and space parts of the pattern having substantially a same width are arranged in a set, and the deformation amount is determined such that deformation amounts of the pattern parts and the space parts have a same value in the set.

* * * * *